United States Patent
Dobson, Jr. et al.

(10) Patent No.: US 6,423,327 B1
(45) Date of Patent: Jul. 23, 2002

(54) TREATMENT OF SKIN WITH ADENOSINE OR ADENOSINE ANALOG

(75) Inventors: James G. Dobson, Jr., Auburn; Michael F. Ethier, Grafton, both of MA (US)

(73) Assignee: University of Massachusetts, Boston, MA (US)

(*) Notice: Subject to any disclaimer, the term of this patent is extended or adjusted under 35 U.S.C. 154(b) by 0 days.

(21) Appl. No.: 09/672,348

(22) Filed: Sep. 28, 2000

Related U.S. Application Data

(63) Continuation of application No. 09/179,006, filed on Oct. 26, 1998, now abandoned.

(51) Int. Cl.$^7$ ................................................ A61K 7/00
(52) U.S. Cl. ...................... 424/401; 424/447; 424/448; 424/449; 514/46
(58) Field of Search ........................ 424/407, 447, 424/448, 449; 514/46

(56) References Cited

U.S. PATENT DOCUMENTS

| | | | |
|---|---|---|---|
| 4,088,756 A | 5/1978 | Voorhees .................... 424/180 |
| 4,454,122 A | 6/1984 | Stramentionoli et al. ... 424/180 |
| 5,399,349 A | 3/1995 | Paunescu et al. ......... 424/195.1 |
| 5,460,959 A | 10/1995 | Mulligan et al. ......... 435/172.3 |
| 5,618,544 A | * 4/1997 | Brown ........................ 424/401 |
| 5,770,582 A | 6/1998 | Von Borstel et al. .......... 514/45 |
| 5,785,978 A | * 7/1998 | Porter et al. ................ 424/401 |
| 5,821,237 A | 10/1998 | Bissett et al. .................. 514/75 |
| 5,932,558 A | 8/1999 | Crostein et al. ............... 514/46 |
| 5,998,423 A | 12/1999 | Manneth et al. ............. 514/260 |

FOREIGN PATENT DOCUMENTS

DE 19545107 * 6/1997

OTHER PUBLICATIONS

Hartzshtark et al. The use of indentometry to study the effect of agents known to increase skin cAMP content. Experentia. 41(3), 378–379, 1985.*

Adair et al., "Vascular development in chick embryos: a possible role for adenosine" American Physiological Society; 0363–6135/89 1989.

Ahmed et al., "Presence of Both $A_1$ and $A_2$ Adenosine Receptors in Human Cells and Their Interaction," Biochemical and Biophysical Research Communications, 208:871–878, 1995.

Ethier et al., "Adenosine Stimulation of DNA Synthesis in Human Endothelial Cells," The American Physiological Society, 272:H1470–H1479, 1997.

Grove et al., "Optical profilometry: An objective method for quantification of facial wrinkles," Journal of the American Academy of Dermatology, 21:631–637, 1989.

Gruber et al., "Increased Adenosine Concentration in Blood From Ischemic Myocardium by AICA Riboside," Circulation, 80:1400–1411, 1989.

Kollias–Baker et al., Journal Pharmacology and Experimental Therapeutics, 281: 761–768, 1997.

Newby et al., Critical Evaluation of the Role of Ecto—and Cytosolic 5' Nucleotidase in Adenosine Formation Topics and Perspectives in Adenosine Research, 155–168, 1987.

Olsen et al, "Tretinoin emollient cream: a new therapy for photodamaged skin," Journal of the American Academy of Dermatology, 26:215–224, 1992.

Olsen et al., "Tretinoin emollient cream for photodamaged skin: Results of 48–week, multicenter, double–bir studies," Journal of the American Academy of Dermatology, 37:217–226, 1997.

* cited by examiner

Primary Examiner—Thurman K. Page
Assistant Examiner—Lakshmi Channavajjala
(74) Attorney, Agent, or Firm—Fish & Richardson P.C.

(57) ABSTRACT

Methods for enhancing the condition of non-diseased skin by application of compositions containing adenosine or an adenosine analog are disclosed. Also disclosed are methods for increasing DNA synthesis or protein synthesis in dermal cells, and methods for increasing dermal cell size, by application of compositions containing adenosine.

10 Claims, 2 Drawing Sheets

TREATMENT OF SKIN WITH ADENOSINE OR ADENOSINE ANALOG

This application is a continuation of application Ser. No. 09/179,006, filed Oct. 26, 1998, now abandoned.

STATEMENT AS TO FEDERALLY SPONSORED RESEARCH

Work on this invention was supported by funds from the United States government (Public Health Service Grants HL-22828 and AG-11491). The government therefore has certain rights in this invention.

FIELD OF THE INVENTION

This invention relates to dermatology and cell biology.

BACKGROUND OF THE INVENTION

Skin includes a surface layer, known as the epidermis, and a deeper connective tissue layer, known as the dermis. The epidermis undergoes continuous turnover as the outermost cells are exfoliated and replaced by cells that arise from inner dermal layers. The dermis is composed of a variety of cell types, including fibroblasts.

Skin thickness begins to decline in humans after the age of 20 as the dermis becomes thinner and the number of skin fibroblasts declines. As skin ages, or is exposed to UV light and other environmental insults, changes in the underlying dermis can lead to the functional and morphological changes associated with damaged skin. Decreases in the abundance and function of products of the fibroblasts, which include collagen and proteoglycans, are believed to play major roles in wrinkled and damaged skin.

SUMMARY OF THE INVENTION

We have discovered that adenosine stimulates DNA synthesis, increases protein synthesis, and increases cell size in cultures of human skin fibroblasts. Based on this discovery, the invention provides methods and compositions for enhancing the condition of skin.

In general, the invention provides a method for enhancing the condition of non-diseased skin of a mammal, e.g., a human. The method includes topically applying a therapeutically effective amount of a composition including adenosine or an adenosine analog to non-diseased skin of the mammal.

The invention also provides a method for promoting healing of broken, non-diseased skin in a mammal by topically administering a composition including a therapeutically effective amount of adenosine or an adenosine analog to the mammal.

Also included in the invention is a method for increasing DNA synthesis in a dermal cell of non-diseased skin of a mammal. The method includes topically administering a therapeutically effective amount of adenosine or an adenosine analog to a region of non-diseased skin of the mammal containing dermal cell. The adenosine is added so that it does not cause proliferation of the dermal cell.

The invention also features a method of increasing protein synthesis in a dermal cell of non-diseased skin of a mammal. The method includes topically administering a composition including a therapeutically effective amount of adenosine or an adenosine analog to a region of skin of the mammal containing the dermal cell. The adenosine or adenosine analog does not cause proliferation of the dermal cell.

Also provided in the invention is a method of increasing cell size in a dermal cell in non-diseased skin of a mammal, e.g., a human. The method includes topically administering a composition including a therapeutically effective amount of adenosine to a region of skin of the mammal containing the dermal cell, wherein addition of the adenosine does not cause proliferation of the dermal cell, wherein addition of the adenosine does not cause proliferation of the dermal cell.

The invention also includes a method for enhancing skin condition in a mammal, e.g., a human. The method includes providing fibroblasts from the mammal ex vivo, culturing the fibroblasts in the presence of adenosine, and reintroducing the fibroblasts into the mammal.

The therapeutically effective amount of adenosine used in the above-described methods is preferably $10^{-3}$ M to $10^{-7}$ M, more preferably $10^{-3}$ M to $10^{-6}$ M, and most preferably about $10^{-4}$ M.

The composition used in the above-described methods can include a second agent in addition to adenosine. The second agent can be, e.g. an agent that promotes binding of adenosine or an adenosine analog to an adenosine receptor, an angiogenic factor such as vascular endothelial cell growth factor (VEGF), basic fibroblast growth factor (BFGF), an agent that itself enhances skin condition, such as tretoinin or another known conditioning agent such as an emollient, a humectant, or an occlusive agent.

In preferred embodiments of the invention, the adenosine or an adenosine analog does not promote skin cell proliferation.

The invention also provides a composition including about $10^{-3}$ M to about $10^{-7}$ M adenosine and a therapeutically effective amount of an angiogenesis factor. In some embodiments, the composition of the adenosine is about $10^{-4}$ M.

As. used herein, "enhancement of skin condition" means a noticeable decrease in the amount of wrinkling, roughness, dryness, laxity, sallowness, or pigmentary mottling in skin.

As used herein, a "therapeutically effective amount" of adenosine or an adenosine analog means an amount that enhances skin condition when applied to skin.

As used herein, "non-diseased skin" means skin free of any proliferative disorder observable by visual inspection.

The present invention advantageously allows for enhancement of skin condition. This results in skin that shows a less wrinkled, rough, or dry complexion. For example, the invention provides for enhancing the condition of skin damaged due to exposure to the sun or skin whose condition has deteriorated due to normal aging.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of this invention will be apparent from the following description of-the preferred embodiments thereof, and from the claims.

DETAILED DESCRIPTION

Figure 1A:
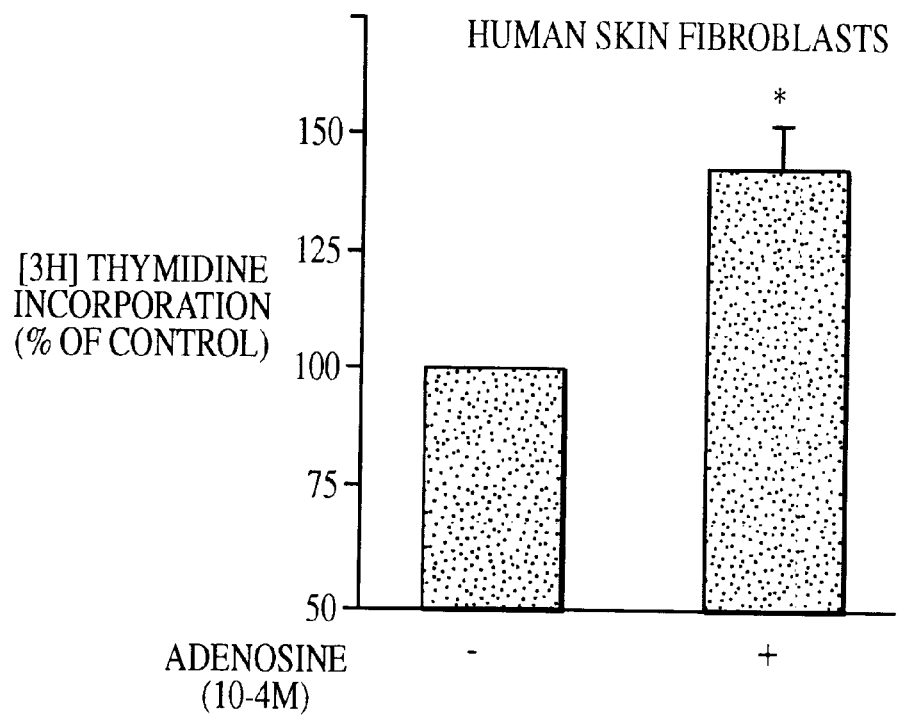
FIGS. 1A and 1B are histograms showing the effect of adenosine on [$^3$H]thymidine incorporation in cultures of normal human skin (FIG. 1A) and lung fibroblasts (FIG. 1B). After incubation in serum-free medium for 24 hours, cells were exposed to $10^{-4}$ M adenosine for 18 hours. Medium was replaced with serum-free medium without adenosine, and [$^3$H]thymidine was added. Results are expressed as percent [$^3$H]thymidine incorporation compared to control cultures without adenosine and are means±SEM for 4–5 experiments. "*" denotes value was significantly different from control value without adenosine.

The invention is suitable for treating skin of a mammal, e.g., a human, for which promotion of fibroblast-associated dermal functions is desired. For example, promotion of fibroblast-associated functions is desirable in enhancing the condition of aged skin, which is associated with a decrease in dermal cell function and is characterized by increased dryness or roughness, or both. The method can also be used on subjects having otherwise damaged skin, e.g., wrinkled skin and skin with a non-proliferative disorder. The method can may further be used prophylactically on a subject to minimize deterioration of skin condition associated with aging or environmental factors, such as photodamage.

Adenosine and suitable adenosine analogs are suitable for use in enhancing skin condition. Adenosine analogs such as adenosine agonists, adenosine receptor agonists, and compounds that increase intracellular or extracellular adenosine levels are suitable for use in the invention.

Agonists of adenosine include 2'-deoxyadenosine; 2', 3'-isopropoylidene adenosine; toyocamycin; 1-methyladenosine; N-6-methyladenosine; adenosine N-oxide; 6-methylmercaptopurine riboside; 6-chloropurine riboside, 5'adenosine monophosphate, 5'-adenosine diphosphate, or 5'-adenosine triphosphate. Adenosine receptor agonists include phenylisopropyl-adenosine ("PIA"), 1-Methylisoguanosine, ENBA (S(-), $N^6$-Cyclohexyladenosine (CHA), $N^6$-Cyclopentyladenosine (CPA), 2-Chloro-N6-cyclopentyladenosine, 2-chloroadenosine, and adenosine amine congener (ADAC), all of which are agonists for the adenosine $A_1$ receptor. Other receptor agonists include 2-p-(2-carboxy-ethyl) phenethyl-amino-5'-N-ethylcarboxamido-adenosine (CGS-21680), N-ethylcarboxamido-adenosine (NECA) and napthyl-substituted aralkoxyadenosine (SHA-082), 5' (N-Cyclopropyl)-carboxamidoadenosine, DPMA (PD 129, 944), Metrifudil, which are agonists for the adenosine $A_2$ receptor. Other adenosine receptor agonists include those which preferentially bind the $A_1$ receptor relative to the $A_2$ receptor, such as 2-Chloroadenosine, $N_6$-Phenyladenosine, and $N^6$-Phenylethyladenosine; and those which preferentially bind the $A_2$ receptor relative to the $A_1$ receptor, such as 2-Phenylaminoadenosine and MECA.

Also suitable for use are compounds that increase intracellular adenosine concentration by inhibiting the cellular uptake of adenosine or the breakdown of adenosine. One pathway of adenosine metabolism is the conversion of adenosine to inosine by adenosine deaminase. An example of an adenosine deaminase inhibitor is erythro-9-(2-hydroxy-3-nonyl) adenine ("EHNA"). Adenosine kinase inhibitors can also be used. Adenosine kinase converts adenosine to adenosine monophosphate by adenosine kinase. An example of an adenosine kinase inhibitor is iodotubercidin. Other suitable compounds include those that inhibit the dipyridamole-sensitive nucleoside transporter, which exports adenosine from the cytoplasm, and agents that promote the activity of a 5'-nucleotidase, e.g., the ATP-activated 5'-nucleotidase, which forms adenosine. Compounds that increase tissue adenosine and ATP levels include acadesine (AICA-riboside), which is described in Gruber et al., Circulation 80:1400–1411 (1989).

Adenosine can be also be administered with a second compound. The second compound can enhance the action of adenosine or the adenosine analog, e.g., by enhancing binding of adenosine or an adenosine analog to an adenosine receptor. An example of such a compound is PD 81, 728, which is described in Kollias-Baker et al. J. Pharmacol. Exp. Ther. 281:761–68. Alternatively, the second agent can itself act to enhance skin condition. Examples of these types of agents include tretinoin, a recognized skin conditioning agent (see, e.g., Olsen et al., J. Amer. Acad. Dermatol. 37:217–26, 1997), an angiogenic factor such as vascular endothelial cell growth factor (VEGF) or basic fibroblast growth factor (BFGF), or a conditioning agent.

The second compound can also be a conditioning agent such as an emollient, humectant, or occlusive agent. Numerous examples of particular conditioning agents are provided in the CTFA Cosmetic Ingredient Handbook (Cosmetic Toiletries and Fragrances Association, Washington, D.D., 1988). Emollients help to maintain the soft, smooth, and pliable appearance of skin and function by remaining on the skin surface or in the stratum corneum to act as lubricants, to reduce flaking, and to improve the skin's appearance. Examples of emollients include acetyl trioctyl citrate, cetyl alcohol, butyl myristate, cetyl alcohol, and mineral oil.

Humectants act to increase the water content of the top layers of the skin. Humectants include, e.g., acetamide MEA, fructose, and xylitol. Occlusive agents inhibit the evaporation of water from skin, thereby increasing the water contend of the skin. Acetylated castor oil, mineral oil, and lauryl stearate are examples of occlusive agents.

A subject can be treated by applying adenosine or an adenosine analog in a pharmaceutical composition in an effective amount and for a period of time sufficient to improve the condition of the skin.

The pharmaceutical composition may be formulated using conventional methods to prepare pharmaceutically useful compositions. Such compositions preferably include at least one pharmaceutically acceptable carrier, such as those described in Remington's Pharmaceutical Sciences (E. W. Martin). In addition, the compositions preferably include a pharmaceutically acceptable buffer, preferably phosphate buffered saline, together with a pharmaceutically acceptable compound for adjusting isotonic pressure, such as, for example, sodium chloride, mannitol, or sorbitol.

Adenosine or an adenosine agonist can also be provided in carriers and adjuvants such as ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances and polyethylene glycol. Adjuvants for topical or gel base forms of adenosine or adenosine analogs may, for example, be selected from the group consisting of sodium carboxymethylcellulose, polyacrylates, polyoxythylene-polyoxypropylene-block polymers, polyethylene glycol and wood wax alcohols. For all administrations, conventional depot forms may be used.

The adenosine or adenosine analog-containing compositions may be in any pharmaceutically acceptable dosage form. They are preferably applied by topical routes to exert local therapeutic effects. For topical application, the penetration of the adenosine into skin tissue may be enhanced by a variety of methods known to those of ordinary skill in the art. For example, adenosine may be applied directly and mechanically rubbed into the skin. Alternatively, adenosine or adenosine analogs may be incorporated into a transdermal patch that is applied to the skin. Preferably, the penetration resulting from these methods is enhanced with a chemical transdermal delivery agent such as dimethyl sulfoxide (DMSO) or the nonionic surfactant, n-decylmethyl sulfoxide (NDMS), as described in Choi et al., Pharmaceutical Res., 7(11):1099, 1990.

Other modes of administration include, e.g., oral, subdermal, intradermal, or intravenous. When oral administration is used, it is critical that the adenosine or adenosine analog be delivered to that it is not degraded prior to exiting the digestive system.

The most effective mode of administration and dosage regimen of adenosine or the adenosine analog will depend upon the skin condition, previous therapy, the subject's health status, response to the adenosine, the judgment of the treating physician and the mode in which the adenosine is applied. For example, dosages for a therapeutically effective amount for topical application would be in the range of 100 ng to 10 mg per treated surface area per day. The adenosine may be administered to the patient at one time or over a series of treatments. When adenosine or the adenosine analog is administered in conjunction with a second agent, they can be administered either concurrently or sequentially, and can be administered in the same mode or a different mode, e.g., topical or oral.

Adenosine or an adenosine analog enhances skin condition when there is a noticeable decrease in noticeable decrease in the amount of wrinkling, roughness, dryness, laxity, sallowness, or pigmentary mottling of the treated skin. Methods of measuring improvements in skin condition are well known in the art (see, e.g., Olsen et al., J. Amer. Acad. Dermatol. 26:215–24, 1992), and can include subjective evaluations by the patient or a second party, e.g., a treating physician. Objective methods can include skin topography measurements, such as those described in Grove et al., J. Amer. Acad. Dermatol. 21:631–37 (1989). In skin topography measurements, silicone rubber replicas are made of a small area of skin, e.g., a 1 cm diameter circular area. The silicone rubber replicas capture fine lines and wrinkles on the skin. These specimens are then analyzed using computerized digital image processing to provide an objective measurement of the skin's topography. Skin topography measurements generated following digital-image processing can be measured using the values $R_a$ and $R_z$ as described in Olsen et al., J. Amer. Acad. Dermatol. 37:217–26, 1997, where $R_a$ represents the area of deviation of skin surface features above and below an average central line, and $R_z$ represents the difference between the maximum and minimum heights in five equal segments of the skin surface profile. A statistically significant decline (e.g., P<0.05) in $R_a$ and $R_z$ values in skin treated with adenosine or an adenosine analog compared to untreated skin indicates an enhancement of skin condition.

Fibroblasts treated with adenosine or adenosine analogs can also be incorporated into a matrix and implanted in the body, e.g., as part of a skin graft. In addition, fibroblasts can be genetically engineered ex vivo to increase the amount of intracellular adenosine levels and then re-introduced into a human patient. (See, for example, Anderson et al. U.S. Pat. No. 5,399,349; and Mulligan & Wilson, U.S. Pat. No. 5,460,959, each of which is incorporated by reference herein in its entirety).

Experimental Information

Cell Culture

Human skin fibroblasts and human lung fibroblasts were supplied by the N.I.A. Aging Culture Repository Center (Camden, N.J.). For skin fibroblasts, primary cultures had been initiated from explants obtained from a 3 mm punch biopsy of the mesial aspect of the upper left arm. Human lung fibroblasts (IMR-90) were established from a 16-week normal female fetus. All cells displayed a normal diploid karyotype and all cells tested negative for bacteria, fungi and mycoplasma contamination.

Cells were grown in Eagle's minimal essential medium (MEM) supplemented with 10% fetal bovine serum (FBS), 100 U/ml penicillin and 100 mg/ml streptomycin in a 37° C., 5% $CO_2$/95% air environment. After reaching confluence, cells were subcultivated with 0.25% trypsin in MEM with no added $Ca^{2+}$ or $Mg^{2+}$.

Incorporation of [$^3$H]Thymidine

As an index of DNA synthesis incorporation of [$^3$H] thymidine was measured as described in Ethier et al., Am. J. Physiol. 272:H1470–79 (1997). Confluent monolayers of human skin fibroblasts in MEM plus 10% FBS were seeded into 16 mm diameter culture wells (24-well plates) at a density of $1 \times 10^4$ cells/cm$^2$. Cells were grown at 37° C. under standard culture conditions (5% $CO_2$–95% air) until they were approximately 75% confluent. Medium was then removed and the cells were made "serum-free" by incubation in MEM with no FBS for 24 hours. Adenosine or vehicle (MEM) was added for an additional 18 hours. This medium was then replaced with fresh MEM, and the cells were pulsed with lmCi/ml [$^3$H] thymidine (6.7 Ci/mmol). After a 2 hour incubation period, the medium was discarded and the cells were rinsed twice with cold (4° C.) Hank's balanced salt solution (HBSS) and incubated for 5 minutes with 0.5 ml cold 10% (w/v) trichloroacetic acid (TCA). The wells were then rinsed with 8% TCA and the TCA-insoluble material was solubilized with 0.5 ml of a solution of 0.2M NaOH and 0.2% sodium decyl sulfate (SDS). The radioactivity of this fraction was determined by standard liquid scintillation spectrometric techniques.

Incorporation of [$^3$H] thymidine was expressed as counts per minute (cpm) of $^3$H per culture. Data in each experiment was derived from 4 identically treated wells. Since the cpm/well exhibited variation between experiments, data representing combined experiments are expressed herein as a percent of their respective mean control value.

Incorporation of [$^3$H]phenylalanine

Incorporation of [$^3$H]phenylalanine was measured as an index of protein synthesis. Human skin fibroblasts were seeded into 24-well culture plates in MEM containing 10% FBS. When cells had grown to approximately 75% confluence the culture medium was replaced with serum-free MEM with or without adenosine. After 48 hours, 2 μCi/ml

[³H]phenylalanine was added to the cultures. Unlabeled phenylalanine (0.36 mM) was also added to equalize concentrations of intracellular and extracellular phenylalanine. After 8 hours, medium was removed and the cells were washed twice with cold (4° C.) HBSS and incubated for 20 minutes in cold 10% (w/v) TCA. Cells were then incubated 5 minutes in 95% ethanol (4° C.) and the TCA-insoluble material was solubilized with a solution of 0.2M NaOH and 0.2% SDS. The radioactivity of this fraction was determined by standard liquid scintillation spectrometric techniques.

Incorporation of [³H] phenylalanine was expressed as cpm of ³H per culture well and data in each experiment were derived from six identically treated wells. Since the cpm/well exhibited variation between experiments, data representing combined experiments are expressed as a percent of their respective mean control value.

Determination of Cell Size

Human fibroblasts in MEM 10% FBS were seeded into 25 cm$^2$ culture flasks at a density of $1\times10^4$ cells/cm$^2$. When the cells had grown to approximately 80% confluence the culture medium was removed and the cells were incubated in serum-free MEM for 24 hours. Adenosine or vehicle (MEM) was added for 18 hours and cells were then washed twice with cold (4° C.) HBSS. Cells were removed with 0.25% trypsin in calcium-and magnesium-free MEM and diluted in cold (4° C.) HBSS for measurement of relative cell size with a fluorescence-activated cell sorter (FACS; Becton Dickinson Vantage). Cell size was determined by forward light scatter on a minimum of $1\times10^4$ cells per experiment.

Experimental Materials

MEM, FBS, penicillin, streptomycin, trypsin, and HBSS were obtained from GIBCO (Grand Island, N.Y.), [³H] thymidine (6.7 Ci/mmol) and phenylalanine, L-ring-2,3,4,5,6-³H ] (92 Ci/mmol) were obtained from Dupont NEN (Boston, Mass.). Adenosine was from Boehringer Mannheim, SDS was from National Diagnostics, (Highland Park, N.J.) and TCA and ethanol were obtained from Fisher Scientific (Pittsburgh, PA).

Data Analysis

Analysis of variance (ANOVA) was used to determine statistical differences between means. The Dunett's test was applied for multiple comparisons as described in Zar, J.H., Biostatistical Analysis. Englewood Cliffs, N.J., Prentice Hall, Inc. pp. 150–153, 1984. In addition, the Wilcoxon test was employed to verify differences between values expressed as a percentage. Differences were considered statistically different when $P<0.05$.

DNA Synthesis

Figure 1B:
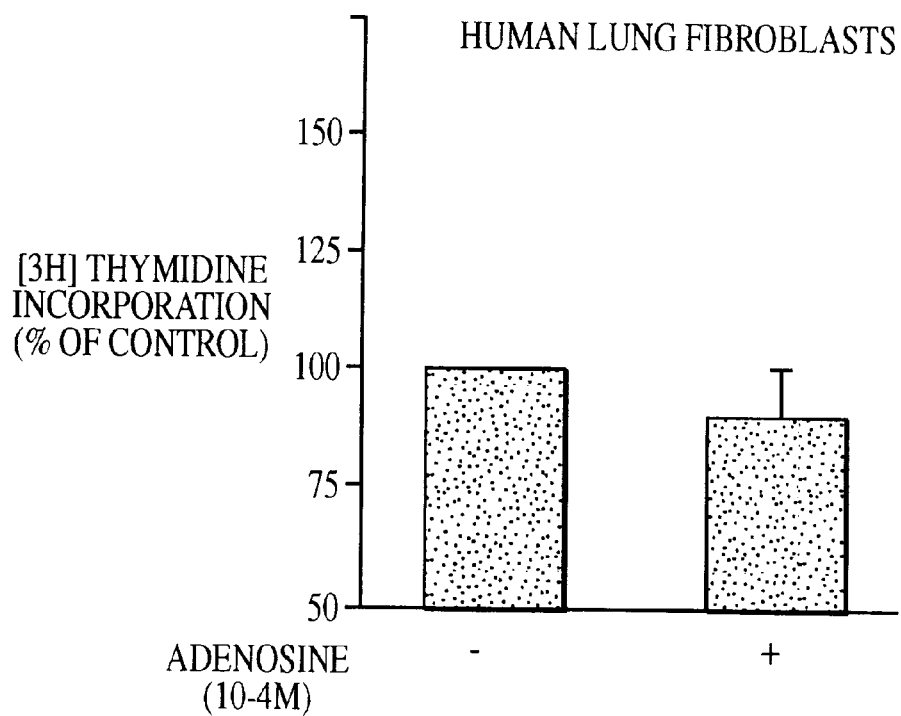

Exposure to 10–4M adenosine increased [³H]thymidine incorporation by 43±9% in five studies on cultures of human fibroblasts (AG607720B) made quiescent by serum removal. These results are summarized in FIG. 1A. In contrast, adenosine ($10^{-4}$M) had no effect on [³H] thymidine incorporation in cultures of human lung fibroblasts (IMR-90) (FIG. 1B). Concentrations of adenosine ranging from 10-7 M to $10^{-3}$ M also failed to stimulate [³H]thymidine incorporation in IMR-90 lung fibroblasts (data not shown).

The effect of adenosine on DNA synthesis was additionally determined on skin fibroblast cultures from six different human donors. Adenosine ($10^{-4}$M) stimulated DNA synthesis in all three cultures derived from young human donors (Table 1). Values shown are means±SEM, where n is number of experiments. Exposure to adenosine and determination of [³H] thymidine incorporation were as described above. The asterisk denotes a value significantly different from the corresponding control (100%).

TABLE 1

Effect of adenosine on [³H] thymidine incorporation into cultured human skin fibroblasts derived from young donors

| Cell Strain | Adenosine ($10^{-4}$M) | Donor Age | Sex | [³H] thymidine incorporation (% of control) | n |
|---|---|---|---|---|---|
| AG07720B | − | 24 | F | 100 | 24 |
|  | + |  |  | 124 ± 7* | 24 |
| AG07306A | − | 28 | F | 100 | 6 |
|  | + |  |  | 193 ± 20* | 6 |
| AG09605 | − | 30 | M | 100 | 12 |
|  | + |  |  | 133 ± 15* | 12 |

Peak stimulation of [³H] thymidine incorporation (93±20%, n=6) was achieved in human skin fibroblast cultures derived from a 28 year old female (AG07306A).

Adenosine ($10^{-4}$M) stimulated DNA synthesis in 2 of 3 cultures derived from aged human donors (Table 2). As in Table 1, values are means±SEM, and n is the number of experiments performed. The asterisk denotes a measurement significantly different from the corresponding control (100%). Adenosine exposure increased [³H] thymidine incorporation by 53±31% and 54±22% in human skin fibroblast cultures derived from a 70 year-old male and a 84 year-old male, respectively. Adenosine had no effect on cultures derived from a 67-year old female.

TABLE 2

Effect of adenosine on [³H] thymidine incorporation into cultured human skin fibroblasts derived from aged donors

| Cell Strain | Adenosine ($10^{-4}$M) | Donor Age | Sex | [³H] thymidine incorporation (% of control) | n |
|---|---|---|---|---|---|
| AG11728 | − | 67 | F | 100 | 6 |
|  | + |  |  | 91 ± 6 | 6 |
| AG12949 | − | 70 | M | 100 | 11 |
|  | + |  |  | 150 + 31* | 11 |
| AG11730 | − | 84 | M | 100 | 10 |
|  | + |  |  | 154 ± 22* | 10 |

Protein Synthesis

Figure 2A:
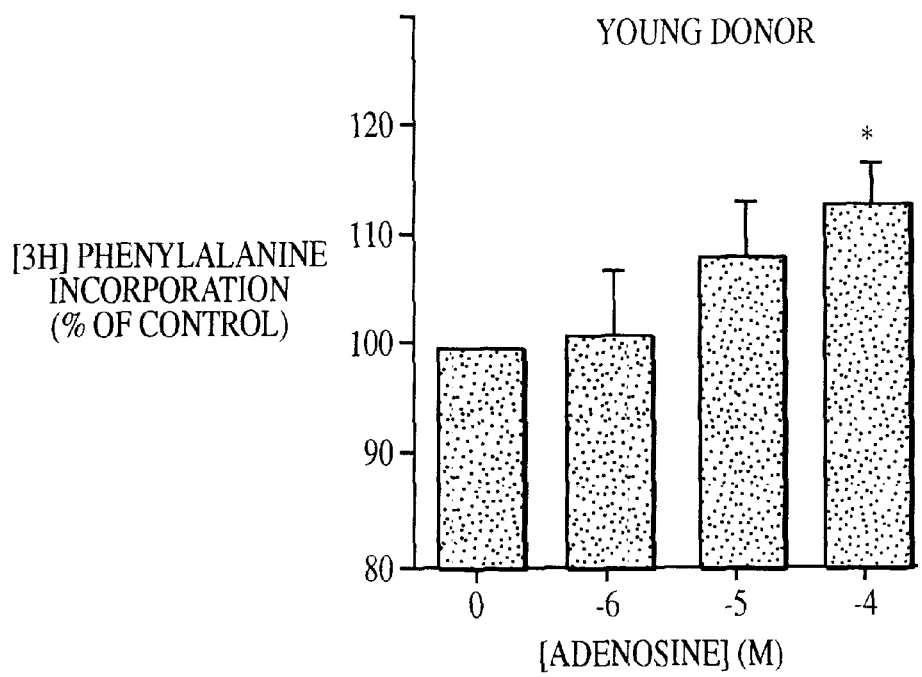
FIGS. 2A and 2B are histograms showing concentration responses of adenosine-stimulated protein synthesis in human skin fibroblasts from a young (FIG. 2A) and aged (FIG. 2B) donor. Cells were grown to 75% confluence. Medium was then replaced with serum-free medium with or without adenosine. After 48 hours, [$^3$H]phenylalanine incorporation was determined as described. Results are expressed as % [$^3$H]phenylalanine incorporation compared to control cultures without adenosine and are means±SEM for 6–25 experiments. "*" denotes value was significantly different from control value without adenosine.
Figure 2B:
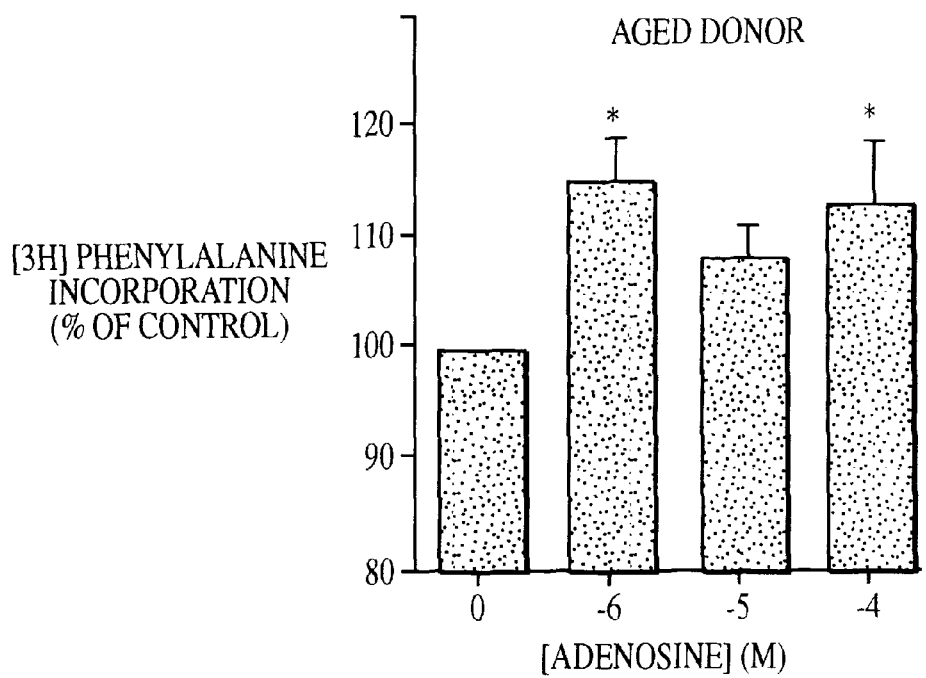

The effect of adenosine on protein synthesis was determined by measuring [³H]phenylalanine incorporation into cultures of human fibroblasts from a young and aged donor. Cultures made quiescent by serum removal were exposed to adenosine ($10^{-6}$M to $10^{-4}$M) for 48 hours and then pulsed with phenylalanine. In skin fibroblast cultures derived from a 28-year old female (AG073060A) and an 84-year old male (AG11730), adenosine($10^{-4}$M) increased protein synthesis by 13±4% (n=25) and 13±6% (n=17), respectively (FIG. 2).

Cell Size

The effect of adenosine on cell size was determined on human skin fibroblasts from young and aged donors by measuring forward light scatter in a FACS analyzer. Cultures made quiescent by serum removal were exposed to adenosine for 18 hours, removed by trypsinization, and diluted in 4° C. HBSS. A minimum of $1\times10^4$ cells were measured for each experiment. The results are shown in Table 2. Values are mean +SEM for relative cell size determined by forward light scatter (FLS) in a fluorescence-activated cell sorter, and n=number of cells measured. The asterisk denotes the measurement is significantly different from corresponding control.

In skin fibroblast cultures from a 28 year old female (AG073060A) adenosine ($10^{-4}$M) significantly increased cell size by 1.8 and 2.2% in two of three experiments (Table 3).

The effect of adenosine on cell size was also measured on skin fibroblasts from an aged donor. The results are shown in Table IV. Values are mean±SEM for relative cell size determined by forward light scatter (FLS) in a fluorescence-activated cell sorter, where n is the number of cells measured. An asterisk indicates a value significantly different from corresponding control.

In cultures derived from an 84-year old male (AG11730), adenosine ($10^{-4}$M) significantly increased cell size by 2.7–4.9% in 3 of 3 experiments (Table 4).

TABLE 3

Effect of adenosine on cell size in cultured human skin fibroblasts derived from young donors

| Experiment Number | Adenosine ($10^{-4}$M) | Relative Size (FLS) | % increase | n |
|---|---|---|---|---|
| 1 | − | 524 ± 0.55 | — | $1.5 \times 10^4$ |
|   | + | 526 ± 0.55 | 0.4 | $1.5 \times 10^4$ |
| 2 | − | 319 ± 1.24 | — | $1.0 \times 10^4$ |
|   | + | 326 ± 1.16* | 2.2* | $1.0 \times 10^4$ |
| 3 | − | 342 ± 0.94 | — | $1.0 \times 10^4$ |
|   | + | 348 ± 0.95* | 1.8* | $1.0 \times 10^4$ |

TABLE 4

Effect of adenosine on cell size in cultured human skin fibroblasts derived from aged donors

| Experiment Number | Adenosine ($10^{-4}$M) | Relative Size (FLS) | % increase | n |
|---|---|---|---|---|
| 1 | − | 333 ± 0.79 | — | $1.0 \times 10^4$ |
|   | + | 342 ± 0.75* | 2.7* | $1.0 \times 10^4$ |
| 2 | − | 323 ± 1.01 | — | $1.0 \times 10^4$ |
|   | + | 337 ± 0.96* | 4.3* | $1.0 \times 10^4$ |
| 3 | − | 306 ± 0.81 | — | $1.0 \times 10^4$ |
|   | + | 321 ± 0.81* | 4.9* | $1.0 \times 10^4$ |

Other Embodiments

While the invention has been described in conjunction with the detailed description thereof, the foregoing description is intended to illustrate and not limit the scope of the invention. For example, while the invention has been described using adenosine and adenosine agonists, other compounds structurally similar to adenosine can also be used, e.g., purine-containing compounds and compounds having a ribosyl moiety. Other aspects, advantages, and modifications of the invention are within the scope of the following claims.

We claim:

1. A method for enhancing the condition of unbroken skin of a mammal by reducing one or more of wrinkling, roughness, dryness, or laxity of the skin, without increasing dermal cell proliferation, the method comprising topically applying to the skin a composition comprising a concentration of adenosine in an amount effective to enhance the condition of the skin without increasing dermal cell proliferation, wherein the adenosine concentration applied to the dermal cells is $10^{-4}$ M to $10^{-7}$ M.

2. The method of claim 1, wherein the composition further comprises an angiogenic factor.

3. The method of claim 1, wherein the adenosine concentration is $10^{-4}$ M to $10^{-6}$ M.

4. The method of claim 1, wherein the adenosine concentration is about $10^{-4}$ M.

5. The method of claim 1, wherein the composition further comprises a conditioning agent.

6. The method of claim 5, wherein the conditioning agent is a humectant, an emollient, or an occlusive agent.

7. The method of claim 1, wherein the mammal is a human.

8. The method of claim 1, wherein the skin comprises a skin graft.

9. The method of claim 1, wherein the composition further comprises a transdermal delivery agent.

10. The method of claim 1, wherein the composition is in a transdermal patch and the composition is topically applied by contacting the patch to the skin.

* * * * *